United States Patent [19]

Alt et al.

[11] Patent Number: 5,788,979

[45] Date of Patent: Aug. 4, 1998

[54] BIODEGRADABLE COATING WITH INHIBITORY PROPERTIES FOR APPLICATION TO BIOCOMPATIBLE MATERIALS

[75] Inventors: Eckhard Alt, Ottobrunn; Axel Stemberger, Neubiberg, both of Germany

[73] Assignee: Inflow Dynamics Inc., Arlington, Va.

[21] Appl. No.: 798,333

[22] Filed: Feb. 10, 1997

Related U.S. Application Data

[63] Continuation-in-part of Ser. No. 632,092, Apr. 15, 1996, abandoned, which is a continuation-in-part of Ser. No. 278,806, Jul. 22, 1994, abandoned.

[51] Int. Cl.$^6$ ........................................ A61F 2/00
[52] U.S. Cl. ...................... 424/426; 523/112; 604/890.1; 604/891.1; 424/400; 427/2.24; 427/2.25; 427/2.26; 427/2.3; 427/2.31; 623/1; 623/6; 623/11; 623/66; 606/154
[58] Field of Search ........................ 424/400, 426; 523/112; 604/890.1, 891.1; 427/2.24, 2.25, 2.26, 2.3, 2.31; 623/1, 6, 11, 12, 66; 606/154

[56] References Cited

U.S. PATENT DOCUMENTS 3,663,288  5/1972  Miller ........................... 128/349
5,019,096  5/1991  Fox et al. ........................ 623/1
5,464,450  11/1995  Buscemi et al. ................ 623/1

FOREIGN PATENT DOCUMENTS

562612  9/1993  European Pat. Off. .

Primary Examiner—Thurman K. Page
Assistant Examiner—Pamela S. Webber

[57] ABSTRACT

A method is disclosed for coating a biomaterial to be placed in contact with a patient's blood flow to inhibit blood coagulation from adhering to the biomaterial that would otherwise result from such contact. A biodegradable material of liquid state compatible with the blood and tissue of the human body is prepared, and an anti-coagulant drug is incorporated into the liquid state of the biodegradable material to form a liquid coating material. The liquid coating material is adhesively applied to a surface of the biomaterial in a substantially continuous overlying layer having a formulation, pattern and thickness selected according to the period of time over which the coating material is to perform its anti-coagulant action. Thereafter the coating material is dried to a layer thickness less than about 100 microns for continuous disintegration thereof as a function of time when the layer is in contact with flowing blood. The method is utilized in an exemplary embodiment in which the biomaterial is a vascular stent.

34 Claims, 2 Drawing Sheets

BIODEGRADABLE COATING WITH INHIBITORY PROPERTIES FOR APPLICATION TO BIOCOMPATIBLE MATERIALS

CROSS-REFERENCE TO RELATED APPLICATION

This application is a continuation-in-part of application Ser. No. 08/632,092, now abandoned, for "Method of Treating Biocompatible Materials for Implantation into the Body of a Patient", filed Apr. 15, 1996, which is a continuation-in-part of application Ser. No. 08/278,806 for "Biodegradable Coating for Biocompatible Materials", filed Jul. 22, 1994, now abandoned.

BACKGROUND OF THE INVENTION

The present invention relates generally to biologically compatible (i.e., biocompatible) materials and devices (collectively, sometimes referred to in this specification as biomaterials) which are implantable into the human body or which merely contact blood or fluids of the body, and more particularly to biodegradable coatings and layers for covering such biomaterials to provide an anti-thrombotic, an anti-stenotic, and/or other related functions.

Some examples of biomaterials adapted to be implanted into the bloodstream or tissue of the human body are intravenous infusion lines, catheters for cardiac catheterization, balloon catheters, electrodes, suture materials, vascular prostheses, and vascular stents. The list is not intended to be exhaustive. The implantation may be acute or long-term, and may be accomplished by insertion of the biomaterial into a blood vessel or vessels of the patient. Alternatively, the biomateral may be used as or in conjunction with apparatus that merely contacts the blood without being implanted or inserted into the body, such as for use in transfusion or dialysis equipment.

In a specific example, it has become common practice to implant a stent in the form of a biocompatible cylindrical metal wire mesh or perforated metal tube in the coronary artery of a patient who has undergone angioplasty, for the purpose of maintaining the arterial lumen open at the site of the angioplasty. In a very brief procedure, the stent is supplied in a compressed condition on, or first compressed by the implanting physician onto, a balloon catheter which is inserted into the patient's vascular system, and the stent is then advanced to the designated site under fluoroscopic observation. The balloon is inflated to deploy the stent by expanding it radially to a diameter which may be slightly larger than the normal unobstructed inner diameter of the arterial wall. Next, the balloon is deflated and the catheter is removed from the patient, leaving the mechanically self-supporting stent in place for permanent retention at the site.

It had been found that a considerable percentage of angioplasty patients suffer restenosis, i.e., another narrowing of the artery wall at the site of the original angioplasty procedure, within a period of only a few months thereafter. For those patients, the practice has been to perform a repeat procedure to re-open the lumen at the designated site. The stent implant procedure was commenced as a prophylactic measure to inhibit re-closure of the lumen following the angioplasty. With recognition that restenosis of the artery may be attributable to intimal hyperplasia, in which trauma to the vessel wall from the angioplasty itself is followed soon thereafter by proliferation of smooth muscle cells, stent implantations have become more commonplace, but the risks of restenosis and thrombosis may, indeed, be exacerbated by the presence of the stent. The pressure exerted by the stent on the vessel wall may increase the trauma that induces the hyperplasia, and the presence of the stent in the blood stream may induce a local or even systemic activation of the patient's hemostase coagulation system.

Bound proteins of blood plasma—principally the adhesive proteins such as albumin, fibronectin, fibrinogen, and fibrin—are known to trigger coagulation. The result is typically the adhesion and aggregation of thrombocytes on the surface of the stent. These proteins include peptide structures, e.g., the RGD-peptides composed of amino acids, such as glycine, arginine, and asparagine. The same structures are involved in the adhesion of thrombocytes as a consequence of receptors of the thrombocyte surface, e.g., collagen, von WilleBrand factor, and fibrin interactions.

The same result may arise with other biomaterials, generally of metal or plastic composition, which are inserted temporarily or implanted permanently in the patient, or which activate the hemostase coagulation system by mere contact with the patient's blood. A risk exists that deployment of a biomaterial and free collagen structures may harm endothelial cells that protect the blood vessel wall, and that a lesion in this area may trigger the adhesion and aggregation of thrombocytes. Thromboplastin released from the cells can also activate the plasmatic coagulation system. The deposit of blood clots on the surface of the biomaterial can result from a complex reaction of plasmatic and cellular mechanisms of coagulation that enhance and influence each other. Unless coagulation is inhibited or existing clots are dissolved, a life-threatening occlusion of the artery may result. Blood clots also trigger the healing of a wound by means of polyploid stem cells.

Thus, for example, the implantation of a stent to keep the lumen of the artery open may only hasten re-occlusion by promoting localized blood clotting and reactive inflammation. Indeed, in vitro and in vivo studies indicate that stents and other untreated biomaterials can be covered with a relatively thick thrombus formation only minutes after contact with blood. Generally, a patient who has undergone a stent implantation is given high doses of anti-coagulants such as heparin, cumarin and/or aspirin to inhibit thrombocyte aggregation and blood clot formation. These and even systemic administration of anticoagulation medications such as hirudin or newly developed GP IIb/IIIa thrombocyte aggregation inhibitors, however, may produce only marginal improvement, and the systemic measures also pose a risk of life-threatening internal bleeding. Acute occlusion of the vessel occurs in 4 to 10% of the cases, and serious bleeding in another 5 to 10% of the cases, despite these measures. The incidence of complications is even more pronounced where the blood vessel diameter is about 3 millimeters (mm) or less, as with the coronary arteries. While instances where the biomaterial is in contact with the blood and/or tissue for only a brief interval are less likely to provoke serious problems, the longer duration and even permanent implants such as vascular stents may require surgical intervention to remove infected material, posing yet another serious risk to the patient. Further, microthrombi at the border between the endothelial structure and the stent stimulate cellular proliferation of the vessel wall.

Another problem arises from absorptive bound proteins of plasma such as albumin, as well as adhesive proteins, which facilitate deposit and adhesion of bacteria from the surface of a catheter used to deploy the stent or other biomaterial, while avoiding detection by the body's immune system because of a build-up of mucus substances. The mucus barrier may be virtually impervious to systemically introduced antibiotics, which decreases the effectiveness of the treatment.

U.S. Pat. No. 4,281,668 describes the coating of a small implantable carbon lead with a thin layer of a hydrophilic ion-conducting polymer assumed to be body and blood compatible, to prevent the generation of thrombi. In a technique described by U.S. Pat. No. 5,103,837, an implanted porous stimulation electrode for a cardiac pacemaker is coated with a thin layer of hydrophilic polymer, and it is known that an anti-inflammatory steroid can be embedded into such polymer. Such approaches depend primarily on affecting the electrical charge on the biomaterial surface, or on embedding anticoagulation medication into non-absorbable or non-degradable polymers, or on fixation of drugs by chemical means. Anticipated benefits have not been achieved, however, because only minor release of the drugs occurs by leaching from the surface of the polymer with the result that the surfaces are rapidly coated with protein deposits and small thrombi. Absorption of proteins inhibits release of the chemically bound drugs, which enhances a build-up of thrombogenic surfaces.

It is a principal aim of the present invention to provide means and methods for the coating of biomaterials in a way that prevents the deposition of thrombi and coagulation deposits following an activation of plasmatic or cellular blood coagulation.

Another aim of the invention is to provide a technique of incorporating anti-coagulative and anti-inflammatory drugs into a coating for biomaterials that will enable a sufficient release of the drug into the surrounding tissue and bloodstream to achieve its intended purpose.

SUMMARY OF THE INVENTION

According to the invention, stents and other biomaterials intended to be inserted temporarily or implanted permanently in the body, or even merely to be placed in contact with the blood for purposes of transfusion, dialysis or otherwise, are coated with a carrier substance or composition that undergoes continuous degradation within the body to self-cleanse the biomaterial surface as well as to release thrombus inhibitors incorporated in the coating. The carrier degrades slowly through hydrolytic, enzymatic or other degenerative processes. Thrombi are prevented from adhering to the biomaterial surface particularly where the added inhibitors undergo slow release with the controlled degradation of the carrier. Blood components including albumin, adhesive proteins, and thrombocytes, are unable to adhere to the biomaterial surface because of the continuous cleansing action along the entire surface.

Some materials suitable for the coating are presently in clinical use for the slow release of drugs, for example, from capsules, tablets, powders, or other galenic preparations after internal application into the gastrointestinal tract, such as gelatin, cellulose and methacrylic acid. Synthetic polymers have been developed which are degradable within the body, for use as drug carriers. Incorporating drugs into carrier substances, and using powders and micro-beads for timed, continuous release, have been described.

Preferably, the coating carrier is a synthetic or naturally occurring biodegradable polymer such as aliphatic and hydroxy polymers of lactic acid, glycolic acid, mixed polymers and blends, polyhydroxybutyrates and polyhydroxyvaleriates and corresponding blends, or polydioxanon, modified starch, gelatine, modified cellulose, caprolactaine polymers, polyacrylic acid, polymethacrylic acid or derivatives thereof, which will not alter the structure or function of the biomaterial. Such biodegradable polymers will disintegrate, with consequent slow release of drugs incorporated therein, while in contact with blood or other body fluids.

According to the invention, the carrier layer is extremely thin and tightly adherent to the surface of the biomaterial. Preferably, the coating is less than about 100 microns (µm) thick, and most preferably, less than ten µm in thickness. Preferably also, the close adhesion of the coating to the biomaterial surface is achieved by preparing a liquid or semi-liquid phase of the selected carrier material, and applying a very thin, paint-like layer (or multiple layers within the predetermined cumulative or composite upper limit of thinness) thereof, with or without coagulation and/or stenosis inhibitor(s) blended therein, to the surface of the biomaterial, by dipping or spraying followed by drying of the carrier.

Also according to the invention, the carrier material is biodegradable so that it disintegrates in a controlled manner (depending on the characteristics of the carrier material and the thickness of the layer(s) thereof) over time, without harm to the tissue, blood or other fluids of the body. The control over time of disintegration is an important factor. In that respect, it should be observed that the biodegradable carrier may be used alone as the coating, without additives, to continuously cleanse the exposed surface as it disintegrates and thus inhibit adhesion of blood components mentioned above thereto. Preferably, however, the coating is formulated with selected anti-coagulant, anti-thrombotic, anti-inflammatory, or anti-stenotic drugs incorporated therein for timed release as the carrier disintegrates, where the timed release also relies on the controlled time of disintegration of the carrier.

The results of the carrier degradation and drug release may be enhanced by use of plural, synergistic substances, e.g., one for inhibiting plasmatic coagulation and another for inhibiting platelet induced, cellular coagulation. Hirudin is a potent thrombin inhibitor which may be incorporated into the carrier, and in tests, only a few fibrin fibers or aggregated platelets were found by scanning electron microscope (SEM) inspection on these coated biomaterials after prolonged contact with blood. Similar results were achieved with natural or synthetic prostaglandin derivative—potent anti-aggregating drugs—substituted for hirudin in the carrier. And when both hirudin and prostaglandin derivative were used, the inspection showed no protein or fibrin or aggregated platelets on the biomaterial after prolonged contact with blood and tissue.

Specific platelet inhibitors that act on the GP IIb/IIIa receptor are especially helpful in preventing platelet activation following coronary interventions. Anti-adhesive peptides, either alone or in combination with the aforementioned anticoagulants, are also effective as coating material, especially with thrombocyte aggregation inhibitors. The presence of adhesive proteins that function as bridging proteins may be mandatory for adhesion and aggregation of thrombocytes. The slow release of inhibitors of thrombocytic aggregation or thrombocyte receptor antagonists additionally prevent adhesion and aggregation. Naturally existing fibrinolytic concentration can dissolve even small amounts of blood clots on the coated biomaterial surface, to continuously self-clean the surface. Fibrinolytic substances such as Urokinase, r-TPA or Streptokinase added to the carrier provide slow release in situations of high risk for blood clotting, such as in stent implantations.

Increased levels of thrombin-anti-thrombin-III-complexes (TAT-complexes) as well as the prothrombin $F_{1-2}$ were found after exposure of uncoated biomaterials to blood, but not when materials coated according to the invention were used. In other experiments, coated and uncoated catheters were implanted into the jugular vein of pigs. The uncoated catheters revealed blood clots at the implant within six hours, whereas no clots were found on the catheters coated with polyglycolic acid polymers. SEM examination of the vascular wall structures in direct contact with the coated biomaterials showed no indication of change in cellular structure of the vessel—no sign of hyperplasia. Even materials coated under non-aseptic conditions showed no sign of infection after insertion into the femoral artery in the animal model, and no evidence of bacterial settlement on the treated biomaterial.

Anti-proliferation substances, including corticoids and dexamethasone, may be incorporated into the coating carrier to slow proliferation of smooth muscle cells at the internal surface of the vascular wall by preventing local inflammation and inducement of clotting by mediators of inflammation. Substances such as tamoxifen and other cytostatic drugs directly interfere with intimal and medial hyperplasia, to slow or prevent restenosis, especially when incorporated into the coating carrier for slow release during biodegradation. Local relaxation of a vessel can be achieved by inclusion of nitrogen monoxide (NO) or other drugs that release NO, such as organic nitrates or molsidomin.

A further aim of the invention is to achieve synergistic effects with a biodegradable coating applied to a biomaterial surface, by combining as additives to the coating carrier, drugs selected for their different, but complementary beneficial actions for a particular patient and application.

The active period of the treated biomaterial may be adjusted by varying the thickness of the active coating and/or other factors affecting the biodegrading process, such as material(s) selected, and the specific time release of incorporated drugs or other substances selected for their beneficial actions. After some period of time (which may be several weeks) in which the biodegradable material has completely disintegrated, unwanted effects continue to be avoided because the foreign body constituting the biomaterial will have been coated by a natural cell or tissue layer.

Coating an electrode for an implantable cardiac pacemaker lead, for example, prevents build-up of scar tissue on the electrode or at the electrode-myocardial tissue interface that could cause an acute increase in the pacing threshold. A similar procedure is followed to reduce thresholds in implantable defibrillator leads, although in that case an anti-coagulation material is preferred as the additive in the coating, in contrast to the anti-inflammatory material used for a pacing lead electrode. Although the biodegradable carrier will disintegrate in a period of a few weeks, unwanted tissue will not be formed after that time, so the desire to obtain low acute threshold without significant chronic increase is achieved.

A further aim of the invention is to provide a biodegradable coating including a carrier from which anti-inflammatory, anti-coagulant or other selected additive is slowly released, for application to electrodes used for cardiac pacing or defibrillation, to prevent an acute increase in the electrical stimulation threshold.

Another feature of the invention resides in applying the biodegradable coating to the biomaterial in multiple, different layers of the same or somewhat different thickness, for prolonged action of the coating and to enable different beneficial actions to occur at predetermined different intervals of time. The layer intended for the most prolonged action may be applied closest to the surface of the biomaterial, whereas the layer desired to produce the greatest near term response may be applied at the outermost position for initial exposure to the blood. For example, in the case of implanting a stent, the desire is to prevent or inhibit early thrombus formation. For that purpose, the top or upper layer, i.e, the layer in initial contact with the blood, should incorporate a highly active anti-coagulation drug for early release. On an interim and longer-term basis, the desire would be to inhibit cellular proliferation in the vessel wall to avoid restenosis, so that a substance to serve that purpose would be in an underlying layer, closer to the surface of the stent. Alternatively, the anti-coagulant or anti-thrombotic layer could be applied at the interior of the stent configuration, in the blood flow path, and the anti-stenotic layer applied at the exterior of the stent configuration, immediately adjacent the arterial wall. Thus, rather than multiple layers, the coating layer could differ in constituency of additive depending upon its particular orientation on the biomaterial configuration.

Although the case of the vascular stent is of particular interest, and will be given greater scrutiny herein, it will be understood that the invention is applicable to a wide variety of biomaterials and biomaterial applications. In addition to restenosis attributable to proliferation of the smooth muscle cells in the vessel wall in response to the trauma of the percutaneous transluminal coronary angioplasty (PTCA) procedure and the deployment of the stent, a matter of major concern is the mechanical or elastic recoil of the vessel wall following expansion of the stent diameter against the wall during deployment, that exacerbates subsequent reduction of the lumen diameter. Stabilization of the vessel wall and prevention of recoil are enhanced by the relatively rigid metal structure and overall configuration of the stent. That is to say, the stent is composed of a material which, together with the configuration of the stent, i.e., its cylindrical mesh or perforated tubular structure, provides a blend of desired rigidity and flexibility to enable expansion during deployment and only very limited return during recoil, i.e., a resistance to recoil that assures stabilization of the vessel wall. Other biomaterials may be composed of metal or plastic material and/or possess a structural configuration that provides such a relatively rigid structure, which, as one skilled in the art will understand in the present context, is intended to mean a capability to resist external forces of compression without necessarily presenting a completely unyielding framework, so as to provide a mechanically stabilizing effect.

Another important aim of the invention is to provide a method and means for preventing closure of the lumen of a blood vessel by implantation of a stent which is adapted and arranged to inhibit early thrombus formation and subsequent restenosis which could otherwise defeat the purpose of the stent to assure relatively unobstructed blood flow through the vessel. Toward that end, the biodegradable coating on the stent should incorporate drugs which, when controllably released, will (1) inhibit activation of thrombin and platelets, and thereby, the factors released from platelets, such as platelet-derived growth factor, basic fibroplastic growth factor, and transforming growth factor (to name several); and (2) prevent hyperplasia that would otherwise occur typically within the three to six months following PTCA.

According to an aspect of the invention, the amount and dosage of the drug(s) incorporated into and released from the biodegradable carrier material is prescribed to suppress the thrombotic and restenotic processes in the locality of the biomaterial possessing the coating, without otherwise affecting the normal systemic functions.

The active period of the coated stent may be adjusted by varying the thickness of the coating, the specific type of biodegradable material selected for the carrier, and the time release characteristics of specific substances incorporated into the carrier. The effective period of the coating is preferably in a range up to about four weeks, and most preferably up to about three months for virtually total disintegration of the biodegradable coating. The undesirable effects of contact with the blood or tissue sought to be prevented by the coating are unlikely to occur thereafter. The acute response is deemed to be most important. The beneficial action of the coating has been demonstrated by one of the applicants herein in an animal study. Fully four weeks after being implanted in sheep, coated stents had kept the coronary arteries in which they were implanted fully open and unobstructed, whereas the coronary arteries in which uncoated stents had been contemporaneously implanted were significantly obstructed.

BRIEF DESCRIPTION OF THE DRAWINGS

The above and other objects, aspects, features and attendant advantages of the invention will become further apparent from the following description of the best mode of practicing the invention, with examples of methods and materials for coatings utilizing anti-thrombotic, anti-inflammatory, anti-coagulant, anti-proliferative, antibiotic, and even cancer-fighting substances, in conjunction with the accompanying drawings, in which.

DETAILED DESCRIPTION OF THE PREFERRED EMBODIMENTS AND METHODS

An exemplary carrier solution is prepared by dissolving 480 milligrams (mg) of a drug carrier, such as poly-D, L-lactid (available as R203 of Boehringer Inc., Ingelheim, Germany) in 3 milliliters (ml) of chloroform under aseptic conditions. In principle, however, any biodegradable coating material that is blood and tissue compatible and capable of being dissolved, dispersed or emulgated, may be used as the carrier agent if, after application, it dries relatively rapid to a self-adhesive lacquer—or paint-like coating, and will subsequently disintegrate in a controlled manner when in contact with the blood or tissue fluids.

Sterile active ingredients may be selectively added to the basic biodegradable carrier solution for the various purposes described above.

EXAMPLE 1

Hirudin impregnated coating material is prepared by dispersing about 24 mg of finely separated hirudin power into the biodegradable carrier solution under aseptic conditions. The mixture is stored at −10° C. for subsequent application. Alternatively, substances analogous to hirudin such as another anti-thrombotic-acting drug may be used, either in a liquid or powder-dispersed form. Also, a hydrophilic pharmaceutical preparation of PEG hirudin (polyethylene glycol bound hirudin) may be used.

EXAMPLE 2

Synthetic prostaglandin derivative (available in Germany under the trade name Iloprost) coating material is prepared by dispersing 48 mg of Iloprost under aseptic conditions into the biodegradable carrier solution. The composition is stored at −10° C. until ready for use.

EXAMPLE 3

Dexamethasone coating material is prepared by introducing 4.8 mg of finely dispersed dexamethasone powder into the biodegradable carrier solution. Alternatively, liquid dexamethasone which is crystalline in solution (available as Fortecortin in Germany), may be used.

EXAMPLE 4

An antibiotic coating material is prepared by dispersing 4.8 mg of gentamicin powder into the biodegradable carrier solution.

EXAMPLE 5

An anti-coagulant coating material is prepared by dissolving 24 mg of heparin powder into the biodegradable carrier solution.

EXAMPLE 6

An anti-thrombotic coating material is prepared by dispersing 50,000 units of urokinase powder into the biodegradable carrier solution.

To apply the coating to a biomaterial such as a stent, the biomaterial is preferably dipped into the sticky liquid coating solution (which may be moderately to highly viscous, depending on desired thickness of the coating), but may alternatively be sprayed (in one or several coats using a thinner) or brushed with the solution, under sterile conditions, at room temperature. The biomaterial is then removed, and the initial liquid dispersion or emulsion form of the coating material is allowed to dry, after which it becomes a thin, adhesive layer on the biomaterial surface. Typical drying time is about one to two minutes. After evaporation of the solvent (e.g., chloroform), the tightly adhesive coating is preferably less than about 100 μm thick, and more preferably less than about 10 μm thick, on the biomaterial surface. The coating may be applied well in advance of the procedure in which the biomaterial is to be used or even just prior to that procedure, and in only one or a plurality of different layers.

In addition to stents, biomaterial applications advantageously using the biodegradable coating of the present invention include vascular prostheses, heart valve prostheses, carbon fiber electrodes, pacemaker electrodes, defibrillation electrodes and patches, diagnostic and therapeutic polymer catheters for angioplasty and cardiology with and without balloon, tubes and containers used in transfusion medicine, the tubing of heart-lung machines, oxygenators, plastic mandrills, intravenous canules, arterial canules, and suture materials. The list is not intended to be exhaustive. The biodegradable coating adheres to substantially all of the usual materials of which such devices are fabricated, without adverse effect on the biomaterial, and disintegrates continuously over time in the blood or other fluid in the tissue of the body. After insertion into the patient's body, the coating undergoes permanent degradation by continuous hydrolytic, enzymatic and/or other degenerative processes.

For mixed in vitro and in vivo testing, a model of an extracorporeal circulation consisted of a canule for insertion in the human cubital vein. A parallel tubing system was connected to the canule, consisting of six 5-cm-long tubes that had been specially prepared for the test. Biomaterials coated in the manner described herein, as well as uncoated, were incorporated into these tubes. By drawing blood samples at the end of the respective tubes, blood flowed by the individual samples. It was determined from the respective syringes with blood samples to investigate biochemical markers of the activated coagulation such as the TAT-complexes and the prothrombin fragments $F_{1-2}$. After contact with blood, the coated and uncoated biomaterials were removed from the vessels (tubing), and macroscopic, microscopic and SEM examination was performed to ascertain any blood clotting. SEM inspection was especially useful to detect fibrin fibers and aggregated thrombocytes.

In vitro tests were performed with plastic mandrills inserted into the femoral arteries of non-coagulated animals. Uncoated mandrills were inserted into the other side of the animal as a control group. After test completion, coated and uncoated biomaterials were removed and examined. Also, the vessel wall that had been in contact with the mandrill was examined by electron microscopy and various histological methods, to assess presence of fibrin deposits, aggregated thrombocytes, and vascular tissue reaction.

The carrier material may be selected from natural or synthetic aliphatic or hydroxy polymers of lactic acid, glycolic acid, or mixed polymers or blends thereof, but is preferably a biodegradable synthetic polymer such as a polyglycolic acid, polyactid, polyhydrodxybutyrate, polyhydroxyvaleriate, polydioxanon, modified starch, gelatin, modified cellulose, polyacrylic acid, or polymethacrylic acid, as well as a derivative or blend thereof Preferably, the carrier incorporates one or more drugs or substances for anti-coagulation, antithrombotic, anti-inflammatory, anti-proliferative, anti-stenotic and/or antibiotic action, according to the needs of the individual patient or the local effect attributable to the presence of the biomaterial in the body. The additive drugs or substances of the coating should be capable of being dissolved or dispersed in a quickly evaporating solution, such as chloroform or methylchloride, to effect fast drying with a low boiling point.

A coating intended to perform multiple actions may comprise a single layer incorporating several different drugs or substances. For example, an anti-coagulant layer may include at least two drugs for simultaneously release during disintegration of the layer to inhibit both plasmatic and thrombocyte-triggered coagulation onto the biomaterial. Alternatively, the coating may comprise several layers of different materials, each layer including a biodegradable carrier incorporating a different substance for a particular desired action. In a multi-layer (or plural sub-layer) composition, the coating might typically employ the layer with the action of earliest desired response as the outermost layer, and the layer with the action of greatest desired duration or last response as the layer closest to the surface of the underlying treated biomaterial (i.e., the innermost layer). The several layers are typically applied one atop the other, although it is feasible that they may lie in juxtaposition in a particular layer, on the biomaterial surface, each layer being selected according to the time line of anticipated thrombotic, inflammatory, and stenotic reaction of the body.

For the open cylindrical structure of a stent to be implanted in a blood vessel, for example, the coating applied to the outer surface of the cylinder or mesh that will face the vessel wall would be intended for inhibiting restenosis, while the coating applied to the inner surface that faces the axis or lumen of the blood vessel would be intended to prevent thrombus formation, to enable control over the specific actions and timed release thereof during disintegration of the carrier. In such a case, the coatings on the two different sides might be applied by spraying, or by dipping with a temporary protective covering on the side which is not to be coated at that time. Clearly, such differences in the coating that depend on a specific orientation of the exposed surface after implantation of the device requires application of the coating accordingly, including the possibility of coating first one side and then the other. As the biodegradable carrier undergoes continuous disintegration, the exposed surface is continuously cleansed which tends to prevent adhesion of platelets, while the constant but local release of the incorporated substance assures that it will perform its intended action in a controlled manner but solely in a region adjacent the stent so as not to interfere in any substantial sense with systemic processes.

The coating may and preferably does incorporate two synergistically active drugs—for example, one of which inhibits plasmatic and the other of which inhibits cellular coagulation—that may be released over time by the biodegrading process of the carrier. The synergistically active substances may be selected, in such a case, to interact with each other and slow the release of each other to effect a prolonged action.

In the case of a coating which is intended to perform anti-inflammatory action, the anti-inflammatory substances incorporated into the biodegradable carrier may be steroids. In other cases, the coating may contain vascular wall relaxants, or cytostatic drugs, for example.

The coating is preferably characterized by a capability for universal application of its formula to the biomaterial by a physician just prior to performing the procedure for the biomaterial insertion into the body. A hermetically sealed solution which is to form the coating may be applied by spraying or painting onto the biomaterial surface at the site of the interventional or operating procedure to be performed. Rather than using a premixed solution, the biodegradable carrier may be supplied to allow the introduction into it of drugs or substances for coatings that may be prescribed and whose formulas can be individually adjusted and blended directly by the physician, according to the respective case, the biomaterial device or apparatus, and intended action. Thus, for example, the biodegradable carrier may be applied in several layers containing prescribed different active ingredients to be time released by the biodegrading process, and for which the attending physician has created his or her own blend for tailoring the coating composition and its action to the individual needs of a patient.

It will be seen, then, that the biodegradable coating of the present invention provides several beneficial results or functions, including a constant, controlled release of the active substance(s); a continual removal of anything which is atop the outer surface of the coating to prevent adherence to it; and the potential for several different layers atop each other and/or different regions of active substances in a single layer.

Figures 1, 2:
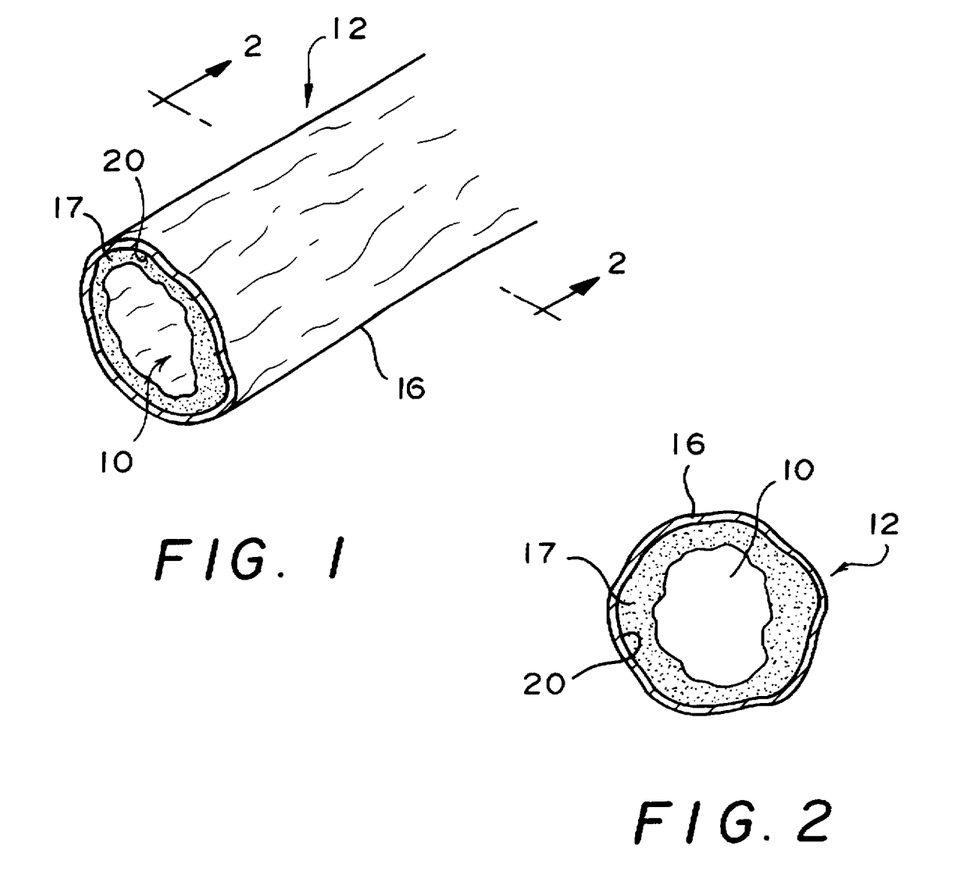
FIG. 1 is a simplified perspective view, partly in section, of a blood vessel.
FIG. 2 is a cross-sectional view of the blood vessel of FIG. 1, taken through a plane containing the lines 2-2 thereof.

Reference will now to be made to the specific case of a vascular stent as the biomaterial. As shown in FIG. 1, a buildup of plaque 17 attributable to deposits of calcified and or fatty substances on the inner surface 20 of the vascular wall 16 has caused a narrowing of the inner lumen 10 of a coronary artery 12 of a patient. A cross-sectional view along a plane through and normal to the longitudinal axis of the artery is illustrated in FIG. 2. The resulting obstruction may cause angina and, if sufficiently severe, can result in an infarction downstream as blood flow through the artery becomes fully or substantially completely impeded.

Figure 3:
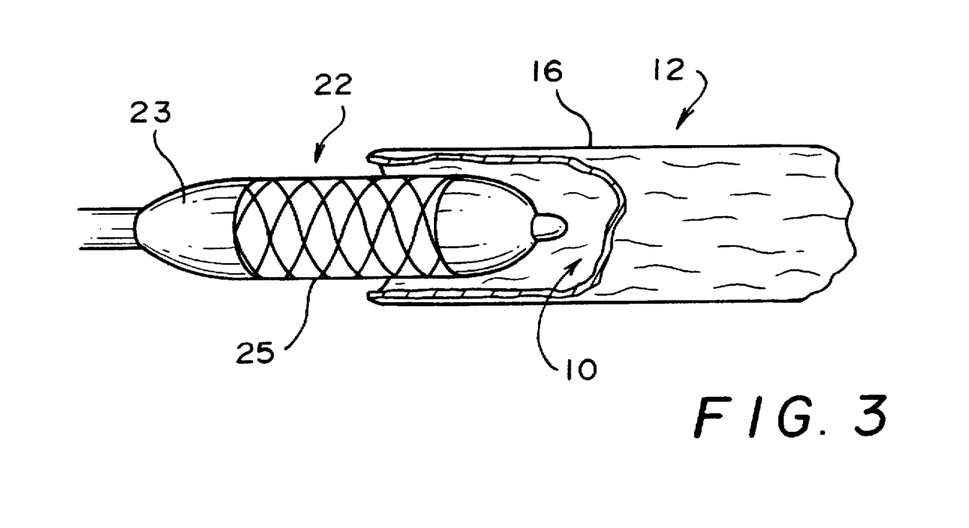
FIG. 3 is a fragmentary side view of the blood vessel of FIGS. 1 and 2, showing the introduction of a balloon catheter and stent therein.

With reference to FIG. 3, a typical procedure for opening the lumen is balloon angioplasty in which a balloon catheter 22 is introduced through a previously inserted guide catheter (not shown) and into the artery 12 until the balloon is properly positioned at the treatment site 15. The angioplasty balloon 23 on the catheter is inflated via a lumen of the catheter to expand sufficiently to compress the plaque against the inner surface of the arterial wall. This increases the diameter of the lumen 10 in the treatment region to permit an adequate flow of blood through the artery to sustain life.

To maintain the lumen open, a stent 25 is implanted at the treatment site. This may be done at the same time as the angioplasty procedure is being performed, by positioning the stent atop the angioplasty balloon, so that when the balloon is inflated to compress the material deposited on the inner surface 20 of the vessel wall 16 it also serves to expand the diameter of the stent 25 to position the stent in intimate contact against the inner surface 20 of the arterial wall. Typically, however, the stent is implanted just after the angioplasty (or atherectomy) procedure is finished. The stent 25 in its expanded state is sufficiently relatively rigid to maintain the expanded diameter and to resist the normal elastic recoil of the vessel wall as shown in exaggerated form in FIG. 4.

Figures 4, 5, 6A:
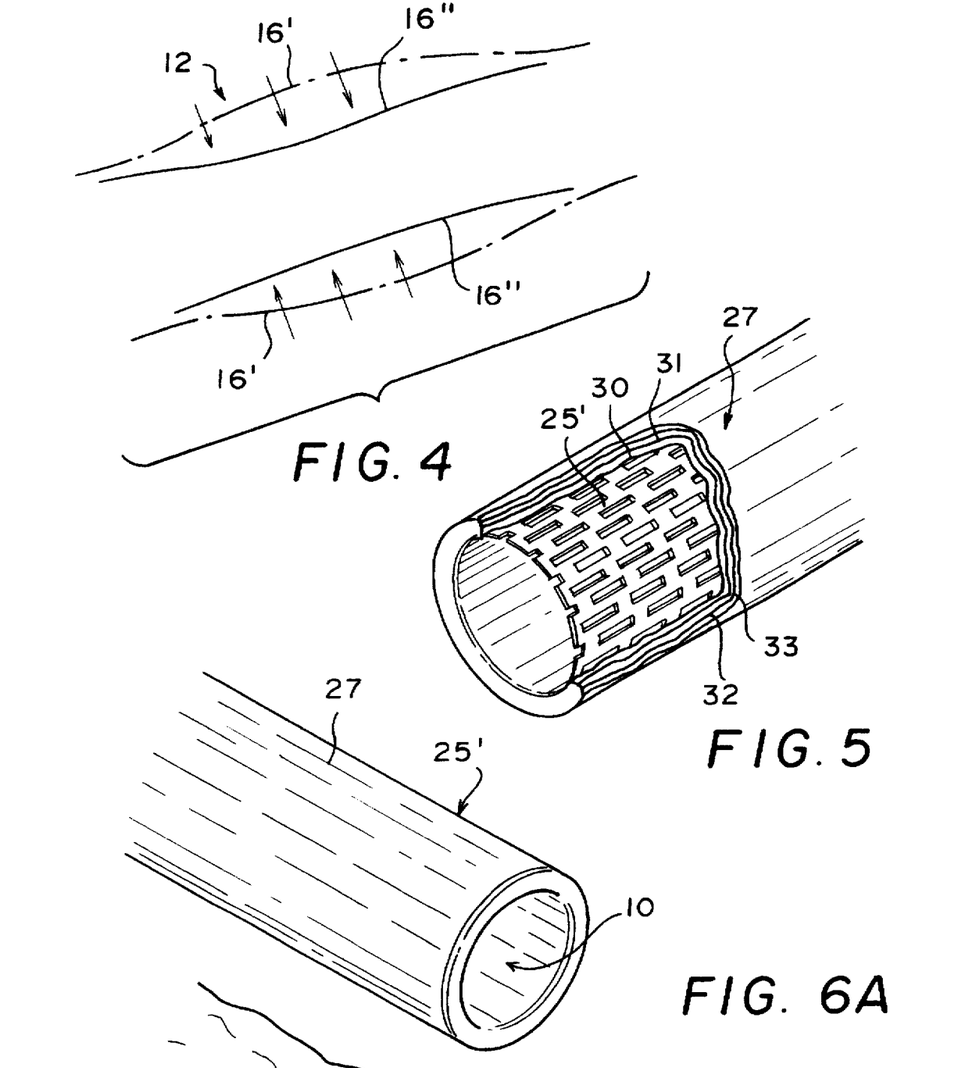
FIG. 4 is a simplified perspective view, partly in section, of the blood vessel alone, indicating the normal, unresisted effect of elastic recoil of the vessel wall following an expanding procedure such as balloon angioplasty.
FIG. 5 is a perspective view of a stent in process of being coated with a biodegradable carrier impregnated with anti-thrombotic, anti-inflammatory, anti-coagulant, anti-proliferative and/or antibiotic substances, in layers, for slow release during disintegration of the carrier.

In FIG. 4, the vessel wall 16' in the expanded state—attributable to the inflation of the angioplasty balloon within the lumen of the vessel—is shown in phantom. After inflation of the balloon to the desired size for compression of the substance on the inner surface of the vessel, the balloon is de-pressurized to place it in negative pressure, and the balloon catheter is removed from the vascular system and the patient's body. The stent, whether it is deployed at the time of the angioplasty or immediately thereafter (using a separate deployment balloon catheter), will remain retained in place against the vessel wall at the treatment site.

The stent should possess sufficient compressive strength, i.e, be relatively rigid, so as to avoid being compressed by the elastic recoil of the artery 12. The recoil, illustrated by the retracted position of the wall at 16", is a response mechanism of the artery wall to having been stretched during lumen expansion by the inflated balloon, perhaps twice—once for the angioplasty and again for the stent deployment. This highlights another problem arising from implantation of a stent; namely, that the ends of the stent which are generally either cut wire or cut tubing with somewhat jagged edges, tend to irritate and inflame the inner surface of the vessel wall at the points of contact therewith. This, too—i.e., as well as the mere presence of the stent tightly against the inner surface of the artery wall—exacerbates the response mechanism of the tissue.

The healing response includes a clotting in which thrombi are formed and attach themselves not only to the traumatized inner surface of the artery wall but also, and preferentially, to the foreign object in the artery—the stent. As the blood contacts the stent material the platelets produce thrombus formations which can quickly lead to a thick covering, especially of the stent's inner surfaces, that produces the beginning of a rapidly expanding, new occlusion of the artery. It is customary, indeed essential, that blood thinners—typically, heparin—are used to prevent or at least lessen the formation of thrombi. But this is an ineffective solution for more than acute processes.

Additionally, restenosis is exacerbated by the presence of the stent, which induces hyperplasia—rapid growth of the smooth muscle cells primarily found in the middle layer of the vascular wall. Inflammation from the initial procedure, presence of the stent against the vessel wall, and elastic recoil of the wall, together muster an action toward narrowing the arterial lumen. Even for an expanded stent 25 (FIG. 3) which is sufficiently rigid to resist recoil of the artery and its effect on occlusion, the other factors are sufficient, if unabated, to result in substantial blockage of the artery in a relatively short time.

This sequence of events can be avoided, and the problems created by the stent itself alleviated, by coating the stent 25 (FIG. 5) in accordance with the present invention as described earlier herein. The biodegradable carrier slowly disintegrates without harmful effect in the cardiovascular system, and in the process, continuously cleanses the exposed surface of the stent (actually, removal of a microscopically thin layer of the coating carrier material) while releasing the drugs incorporated therein. One of the primary requirements for such a carrier to be used in a stent application is that it must be sufficiently elastic and flexible to remain unruptured on the exposed surfaces of the stent despite a considerable expansion of the stent during deployment to increase the lumen diameter from, typically, 1 millimeter (mm) to about 5 mm. To that end, a molecular weight of 27000 dalton of poly-D, L-lactid (the Boehringer Inc. R203 material) for the biodegradable carrier is preferred for meeting the requirements of both mechanical stability and elasticity to attain complete coverage of the stent both in the compressed and expanded states. The carrier material should have a molecular chain length which renders it sufficiently elastic on the stent to preclude cracking or other disruption of the coating when the stent is deployed in the vessel. For example, the stent may have a diameter of 0.03 to 0.04 inch when in the unexpanded state and crimped onto the balloon catheter, and may be expanded to 2.5 to 5 millimeters when deployed, so that it may be stretched by a factor of 3 to 6. The coating must be sufficiently elastic to preclude it from cracking or becoming brittle during such deployment, that any portion of the stent biomaterial is uncoated and exposed. Boehringer R203 has a molecular chain length which is quite adequate for these purposes. Sterile active substances for anti-thrombotic, anti-inflammatory, anti-coagulant, anti-proliferative and/or antibiotic action, and even cancer-fighting capability may be selectively incorporated as desired by addition to the biodegradable carrier solution in the manner previously described herein.

Tight adherence of the carrier to the surface of the metal stent (or other biomaterial) is preferably assisted by applying the carrier material in successive thin layers 30, 31, 32, and 33, as shown in FIG. 5, although fewer or more layers may be used depending on their constituency and whether any layer is a combination. Each layer is applied in a manner described earlier herein, and thereafter is dried before application of the next layer. Particular attention is given to drying of the final layer before the stent 25 with its coating 27 is to be implanted.

The selection of the composition, thickness, and position of each layer, as well as the number of layers, are all factors that determine the timing of release of the drugs in coating 27. For example, an initial release may be set to take place during the first two weeks following implantation, but more likely last the first four or even six weeks. Preferably, the release of anti-stenotic drug(s) should occur over a period of about the first three months. While this corresponds to the period in which restenosis would otherwise take place for any given patient, some contributing effects may be experienced up to about six months after the angioplasty or other procedure for which a stent implant was prescribed.

In carrying out a method of providing the coating, the substance incorporated into the carrier may, for example, be of a type that inhibits thrombin, or that acts on platelet activation, or a combination of agents that acts on plasmatic coagulation and synergistically on platelet activation, with the effect of decreasing the rate of thrombus formation and the rate of restenosis by induction of arteriosclerotic processes as a result of stenting of the blood vessel. The carrier is a preferably a polymer structure for undergoing the continuous disintegration, and the substance may be hirudin for constant release from the coating over time as the polymeric carrier disintegrates. The method may include releasing a quantity of the substance selected to prevent both local thrombosis and late restenosis, in which the dosage of the substance required for preventing restenosis exceeds the minimum dosage required to prevent local thrombosis. The substance may be an anti-proliferative drug, the action of which is enhanced by adding a drug such as tamoxifen, that acts solely on the restenotic process. The substance may be selected to be capable of inhibiting each of thrombus formation, platelet activation, and hyperplasia in the vessel in the locality of the treatment site, such as hirudin, or it may include several different agents, each providing a different one of the inhibitions, while synergistically effective to reduce any toxic effect of the others.

Certain fundamental considerations are applicable in accordance with the invention. For example, the viscosity of the carrier solution is a primary factor in controlling the thickness of the particular layer and the release characteristics of that layer. Also, the molecular chain length of the carrier essentially determines its elasticity, or, stated somewhat differently, selection of a carrier material should be based in part on its elastic properties, which are determined by its molecular weight and chain length. Further, the timed release and disintegration of the carrier is controlled in part by blending together different substances such as polylactic acid and polyglycolic acid having various chain lengths as the carrier.

Figure 6B:
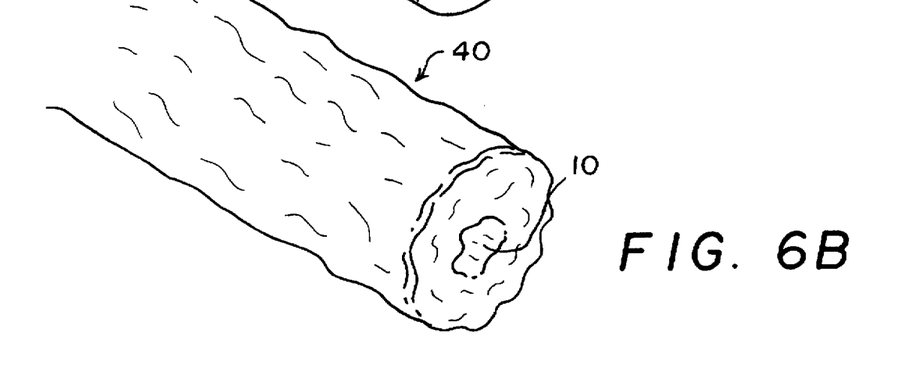
FIG. 6 is a perspective view of a coated stent (in part A) and an uncoated stent (in part B) removed from a coronary vessel of a sheep after having been implanted for about four weeks.

The stark contrast between a stent coated in accordance with the principles of the present invention and an uncoated stent, each of which has been implanted and remained in place in the vascular system of a test animal for a period of time—here, approximately four weeks—is illustrated in FIGS. 6A and 6B. Coated stent 25' of FIG. 6A is remarkably free of the residue of thrombosis, while uncoated stent 40 of FIG. 6B is virtually completely clogged with thrombi. Both stents were implanted in perfectly clean condition, the only difference between the two being the presence or absence of the coating.

Although certain preferred compositions and methods have been disclosed herein, it will be appreciated by those skilled in the art to which the invention pertains, from a consideration of the foregoing description, that variations and modifications may be made without departing from the spirit and scope of the invention. Accordingly, it is intended that the invention shall be limited only by the appended claims and the rules and principles of applicable law.

What is claimed is:

1. A method for coating a biomaterial to be placed in contact with a patient's blood to inhibit blood coagulation on the biomaterial that would otherwise result from such contact, comprising the steps of:

preparing a biodegradable material in a liquid state which is compatible with the blood and tissue of the human body;

incorporating at least an anti-coagulant drug into the liquid state of the biodegradable material to form a liquid coating material; and adhesively applying the liquid coating material to a surface of the biomaterial in a substantially continuous overlying layer having a formulation, pattern and thickness selected according to the period of time over which the coating material is to perform its anti-coagulant action, and thereafter drying the coating material to a layer thickness less than about 100 microns for continuous disintegration thereof as a function of time when said layer is in contact with flowing blood.

2. The method of claim 1, wherein:

said biodegradable material is prepared in a liquid state by inclusion of a solvent therewith.

3. The method of claim 1, wherein:

said coating material further includes at least one additive of a preselected anti-thrombotic, anti-inflammatory, anti-proliferative, anti-stenotic, and antibiotic substance for timed release as the coating material disintegrates when the coated biomaterial is placed in contact with the blood.

4. The method of claim 3, wherein:

said layer is a composite layer including a plurality of sub-layers, each having a formulation, pattern and thickness selected according to the period of time over which the coating material is to perform the action of the respective additive incorporated therein, including one sub-layer incorporating said anti-coagulant drug therein and another sub-layer incorporating said at least one of a preselected anti-thrombotic, anti-inflammatory, anti-proliferative, anti-stenotic, and antibiotic substance therein.

5. The method of claim 4, wherein:

the plurality of sub-layers lie atop one another, with the outermost sub-layer overlying and furthest removed from said surface of the biomaterial incorporating said anti-coagulant drug therein.

6. The method of claim 5, wherein:

the innermost sub-layer is directly overlying and in contact with said surface of the biomaterial and incorporates said anti-stenotic substance therein.

7. The method of claim 4, wherein:

the formulation, pattern and thickness of each of said plurality of sub-layers are selected for a predetermined timed release of the respective additive incorporated in the sub-layer.

8. The method of claim 1, wherein:

said biodegradable material is a biodegradable synthetic polymer selected from the group consisting of polyglycolic acids, polylactids, polyhydroxybutyrates, polyhydroxy-valeriates, polydioxanons, modified starches, gelatins, modified celluloses, polyglycols, polyacrylic acids, polymethacrylic acids, and blends thereof.

9. The method of claim 1, wherein:
said biodegradable material is a natural or synthetic aliphatic or hydroxy polymer of lactic acid, glycolic acid, or mixed polymers or blends thereof.

10. The method of claim 1, wherein:
said layer has a thickness of about 10 microns.

11. The method of claim 1, wherein:
each sub-layer of said composite layer has a thickness of at least about 10 microns.

12. The method of claim 3, wherein:
said layer has at least one region incorporating said anti-coagulant drug therein.

13. The method of claim 12, wherein:
said layer has a second region incorporating said anti-stenotic substance therein.

14. The method of claim 1, wherein:
said biomaterial is selected from the group consisting of a stent, a vascular prostheses, a heart valve prosthesis, a carbon fiber electrode, a pacemaker electrode, a defibrillation electrode, a polymer catheter, tubing used in blood transfusion apparatus, tubing used in a heart-lung machine, an oxygenator, a plastic mandrill, an intravenous canule, an arterial canule, and a suture material catheter.

15. The method of claim 13, wherein:
said biomaterial is a vascular stent of tubular configuration, and said at least one region includes the inner surface of the tubular configuration, and said second region includes at least the outer surface of the tubular configuration.

16. The method of claim 1, wherein:
said liquid coating material is adhesively applied to said biomaterial by painting it on said surface thereof.

17. The method of claim 1, wherein:
said liquid coating material is adhesively applied to said biomaterial by spraying it on said surface thereof.

18. The method of claim 1, wherein:
said liquid coating material is adhesively applied to said biomaterial by dipping said biomaterial into the liquid coating material.

19. The method of claim 1, including:
incorporating a plurality of drugs into the liquid state of said biodegradable material to form the liquid coating material, said plurality of drugs being selected for synergism and each with a desired function and time release characteristic.

20. The method of claim 1, wherein:
said biomaterial is a cardiac electrode adapted to be implanted in the body for use in at least one of stimulating and sensing the heart.

21. The method of claim 1, wherein:
said anti-coagulant drug includes at least two drugs for simultaneously release during disintegration of the coating material layer to inhibit both plasmatic and thrombocytetriggered coagulation onto the biomaterial.

22. The method of claim 1, wherein:
said biomaterial is a vascular stent of tubular configuration, and said layer is composed of material selected to render the layer sufficiently elastic to maintain its integrity despite change in the dimensions of the surface of the stent on which said layer resides during deployment of the stent in a blood vessel.

23. The method of claim 22, wherein:
the biodegradable carrier material is selected to possess a molecular weight and molecular chain length to provide the layer with said sufficient elasticity.

24. A biomaterial device adapted to be placed in contact with human blood in connection with a medical, surgical, therapeutic, restorative, prosthetic, or pathological procedure; said device comprising:
a biomaterial; and
a thin, adhesive layer of material coating a surface of the biomaterial for continuous disintegration as a function of time when said layer is in contact with blood, said layer including:
a biodegradable carrier material having biological compatibility with blood and tissue of the human body, and
a substance incorporated in said carrier material and having at least one inhibitory property selected from the group consisting of anti-coagulant, anti-thrombotic, anti-inflammatory, anti-proliferative, anti-stenotic, and antibiotic, for timed release from said biodegradable carrier material with disintegration thereof when said device has been introduced into the body of the patient,
said layer having a formulation, pattern and thickness selected according to the period of time over which said incorporated substance is to perform its inhibitory property action, said layer thickness being less than about 100 microns.

25. The biomaterial device of claim 24, wherein:
said biomaterial is a vascular stent of tubular configuration, and said layer is composed of material selected to render the layer sufficiently elastic to maintain its integrity despite change in the dimensions of the surface of the stent on which said layer resides during deployment of the stent in a blood vessel.

26. The biomaterial device of claim 25, wherein:
the biodegradable carrier material is s elected to possess a molecular weight and molecular chain length to provide the layer with said sufficient elasticity.

27. A method of providing a vascular stent of tubular configuration with the capability of localized action when deployed at a treatment site of an earlier procedure for opening the lumen of a blood vessel of a patient, wherein said action is to prevent both early thrombus formation on the stent and late restenosis attributable to the lumen opening procedure in the locality of the treatment site, without producing any other substantial systemic effects on the patient, said method comprising the steps of:
preparing a liquid solution of biodegradable material having biological compatibility with blood and tissue of the human body, together with a substantially inert solvent;
adding an anti-thrombotic substance to said liquid solution of the biodegradable material to produce a liquid coating material;
adhesively applying the liquid coating material to an interior surface of the stent tubular configuration in a substantially continuous layer overlying said interior surface and having a formulation, pattern and thickness selected according to the period of time over which the coating material is to perform its anti-thrombotic action, and thereafter drying the coating material to a layer thickness less than about 100 microns for continuous disintegration thereof as a function of time when said stent layer is in contact with flowing blood;
preparing a second liquid solution of said biodegradable material together with said substantially inert solvent;
adding an anti-stenotic substance to said second liquid solution of biodegradable material to produce a second liquid coating material;

adhesively applying the second liquid coating material to an exterior surface of the stent tubular configuration in a substantially continuous layer overlying said exterior surface and having a formulation, pattern and thickness selected according to the period of time over which the second coating material is to perform its anti-stenotic action, and thereafter drying the second coating material to a layer thickness less than about 100 microns for continuous disintegration thereof as a function of time when said layer is in contact with flowing blood.

28. The method of claim 27, wherein:

at least one of the layers of first-mentioned and second coating material further includes at least one additive selected from the group consisting of anti-coagulant, anti-inflammatory, anti-proliferative, and antibiotic substances for timed release as the respective coating material disintegrates when the coated stent is placed in contact with the flowing blood.

29. The method of claim 27, wherein:

said biodegradable material is a biodegradable synthetic polymer selected from the group consisting of polyglycolic acids, polylactids, polyhydroxybutyrates, polyhydroxy-valeriates, polydioxanons, modified starches, gelatins, modified celluloses, polyglycols, polyacrylic acids, polymethacrylic acids, and blends thereof.

30. The method of claim 27, wherein:

said biodegradable material is a natural or synthetic aliphatic or hydroxy polymer of lactic acid, glycolic acid, or mixed polymers or blends thereof.

31. The method of claim 27, wherein:

each of said layers of first-mentioned and second coating material has a thickness of about 10 microns.

32. The method of claim 27, wherein:

each of said layers of first-mentioned and second coating material includes biodegradable carrier material selected to render the respective layer sufficiently elastic to maintain its integrity despite change in the dimensions of the surface of the stent on which said respective layer resides during deployment of the stent in a blood vessel.

33. The method of claim 32, wherein:

the biodegradable carrier material is selected to possess a molecular weight and molecular chain length to provide the respective layer with said sufficient elasticity.

34. The method of claim 27, wherein said any anti-stenotic substance comprises tamoxifen.

* * * * *